United States Patent [19]

Burns

[11] 4,375,815
[45] Mar. 8, 1983

[54] RETRACTABLE LANCET ASSEMBLY

[75] Inventor: James A. Burns, Elizabeth, N.J.

[73] Assignee: Becton Dickinson and Company, Paramus, N.J.

[21] Appl. No.: 246,522

[22] Filed: Mar. 23, 1981

[51] Int. Cl.³ .............................................. A61B 17/34
[52] U.S. Cl. ................................ 128/314; 128/218 F; 128/329 R
[58] Field of Search ................... 128/314, 315, 329 R, 128/329 A, 330, 638, 218 A, 218 F, 253

[56] References Cited

U.S. PATENT DOCUMENTS

| 55,620 | 6/1866 | Capewell | 128/329 R |
|---|---|---|---|
| 1,135,465 | 4/1915 | Pollock | 128/314 |
| 3,030,959 | 4/1962 | Grunert | 128/329 R |
| 3,208,452 | 9/1965 | Stern | 128/315 |
| 4,120,303 | 10/1978 | Villa-Massone et al. | 128/330 |
| 4,139,011 | 2/1979 | Benoit et al. | 128/329 R |
| 4,185,635 | 1/1980 | Burford et al. | 128/330 |
| 4,203,446 | 5/1980 | Hofert et al. | 128/329 R |

FOREIGN PATENT DOCUMENTS 124247  3/1949  Sweden ........................... 128/329 R

OTHER PUBLICATIONS

Sutor et al., "Bleeding From Standardized Skin Punctures", A.J.C.P., vol. 55, May 1971.

*Primary Examiner*—Michael H. Thaler

[57] ABSTRACT

A retractable lancet assembly includes a housing and a sharp-pointed lancet movably mounted inside the housing. A movable sleeve is adapted to urge the lancet point in a direction outwardly from the housing. This sleeve and surfaces on the housing contribute to automatically retracting the lancet point inwardly of the housing responsive to movement of the sleeve in the same direction that the sleeve urges the lancet point outwardly.

9 Claims, 6 Drawing Figures

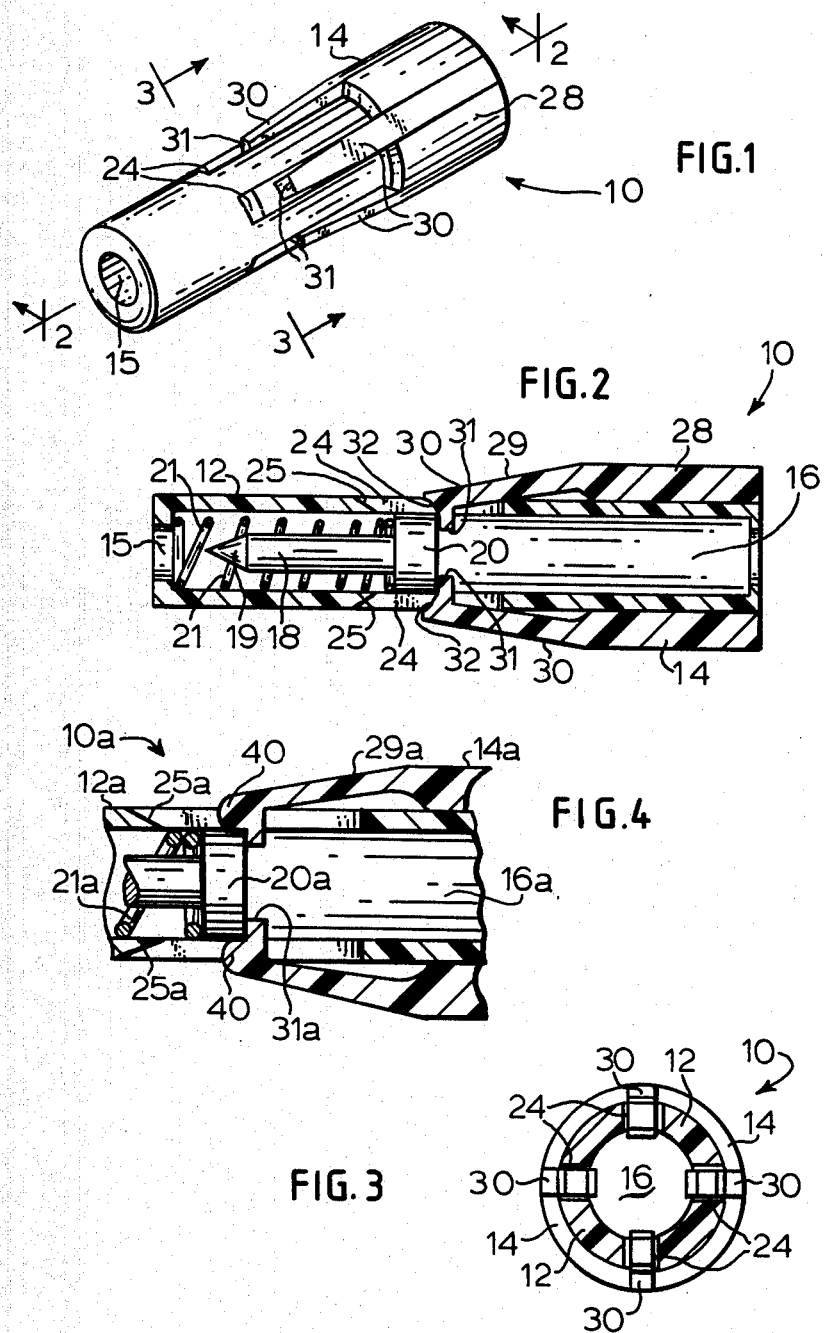

RETRACTABLE LANCET ASSEMBLY

BACKGROUND OF THE INVENTION

1. Field of the Invention.

The present invention relates to a lancet assembly, and more particularly, concerns a retractable spring lancet assembly useful in penetrating the skin of a patient.

2. Description of the Prior Art.

Sharp-pointed lancets are employed to make a quick puncture or penetration of the patients's skin in order to provide a small outflow of blood. Various tests may be employed with only small amounts of blood so that the blood flowing from a finger prick is normally sufficient. However, due to the sensitive nerve endings in the fingertip area, this procedure could induce a significant amount of pain in the patient even though the skin puncture produces minimal cutting. In order to minimize potential pain, it is desirable to make the thrust of the lancet through the patient's skin rapidly.

Spring-loaded lancets of different types and forms have been well known and are typified, for example, by U.S. Pat. Nos. 55,620; 1,135,465; 3,030,959; 4,139,011; 4,203,446; Swedish Pat. No. 124247 and Sutor, A. H. et al., "Bleeding From Standardized Skin Punctures: Automated Technique for Recording Time, Intensity, and Pattern of Bleeding," A.J.C.P., Volume 55, May 1971. Despite the foregoing inventions, improvements in this field of lancets are still being sought.

SUMMARY OF THE INVENTION

A retractable lancet assembly comprises a housing and a sharp-pointed lancet movably mounted inside the housing. Movable means urges the lancet point in a direction outwardly from the housing, and means is provided for automatically retracting the lancet point inwardly of the housing responsive to movement of the movable means in the aforementioned direction.

In a preferable embodiment of the present invention, the assembly includes a coil spring positioned inside the housing for maintaining the lancet within the housing when the spring is in the substantially non-compressed condition. The housing preferably includes a plurality of elongate openings around its periphery, each opening being through the side wall of the housing in proximity to the lancet therein. A slidable sleeve is positioned on the outside of the housing having a plurality of inwardly projecting feet in substantial alignment for projection through the openings. These feet are adapted to engage the lancet upon movement of the sleeve, preferably in the downward direction. Furthermore, in one embodiment of the present invention, inclined mating surfaces are provided on the sleeve and the housing in order to remove the urging force on the lancet after the spring has been compressed. In this fashion, the spring is allowed to become non-compressed thereby automatically retracting the point of the lancet back inside the housing.

In accordance with the principles of the present invention, the lancet makes quick penetration through the skin of the patient and, in the same movement which causes penetration the lancet is allowed to quickly retract back into the housing so that it does not dwell for any substantial length of time in the patient's finger. Also, this lancet can be made to jam after use so that it cannot be re-used and therefore cause contamination. The retractable lancet is conveniently made of very few components, is disposable and thereby economical, is convenient to use and functions rapidly so that discomfiture to the patient can be minimized. Sterile packaging can also be accomplished.

BRIEF DESCRIPTION OF THE DRAWINGS

FIG. 1 is a perspective view illustraing the preferred embodiment of the retractable lancet assembly of the present invention;

FIG. 2 is a cross-sectional view taken along line 2—2 of FIG. 1;

FIG. 3 is a cross-sectional view taken along line 3—3 of FIG. 1;

FIG. 4 is a fractional cross-sectional view illustrating an alternate embodiment of the slidable sleeve;

DETAILED DESCRIPTION

Figure 6:
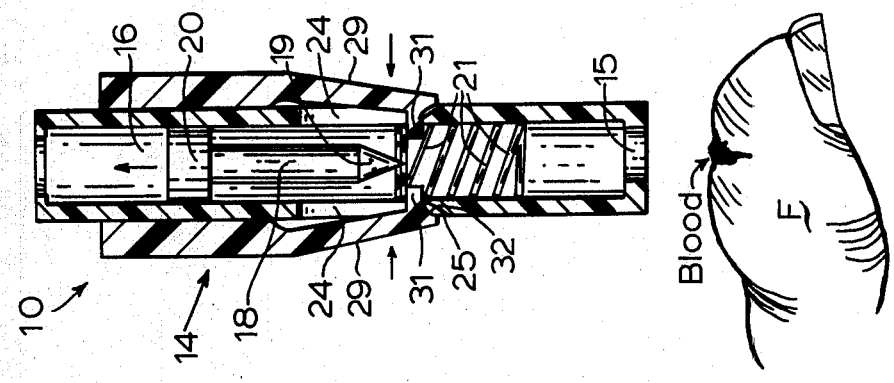
FIG. 6 is a sectional view in sequence from FIG. 4 illustrating the continued operation of the assembly but showing that the lancet point has retracted back inside the assembly out of the patinet's finger.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIG. 1 in particular, there is illustrated a retractable spring assembly 10 consisting of two major external components, a housing 12 and a slidable outside sleeve 14. Sleeve 14 is positioned at one end of the housing, which will be referred to as the proximal end of the housing, while an aperture 15 extends through the distal end of the housing.

FIGS. 2 and 3, taken in conjunction with FIG. 1, illustrate in more detail the internal and external components of retractable spring assembly 10. It is noted that housing 12 is preferably substantially cylindrical and hollow so that a passageway 16 extends completely therethrough. Aperture 15 lies in communication with passageway 16. A lancet 18 is positioned inside housing 12 more toward the distal end. Lancet 18 includes a sharp point 19 at its distal end suitable for penetrating the skin of a patient. A flange 20 is at the opposite end of lancet 18 and preferably is sized to provide a smooth sliding fit within passageway 16. A coil spring 21 lies inside housing 12 and is positioned in the passageway between the distal end of the housing and flange 20. Spring 21 is selected so that, when in the non-compressed condition it can maintain the lancet well within the housing so that point 19 is completely covered and protected. Preferably, lancet 18 lies inside the housing so that sharp point 19 is adjacent the interior side of aperture 15, and aligned for movement therethrough.

Housing 12 preferably includes a plurality of slots 24 or other suitable elongate openings around its periphery. These slots are thus through the side wall of housing 12 and provide communication through the housing between passageway 16 and the outside environment. It is noted that slots 24 are located in a central portion along the longitudinal axis of the housing. More specifically, slots 24 are located so that flange 20 on the lancet lies adjacent these slots when spring 21 is substantially non-compressed, as more clearly seen by referring to FIG. 2. While a plurality of slots is preferable in the present invention, it is understood that in the type of embodiment being described, one elongate opening would be sufficient to accomplish the purposes of this invention. The surfaces 25 of slots 24 facing toward the distal end of the housing are inclined, with the slanted surface facing exteriorly.

Sleeve 14 consists of two portions: a slidable portion 28 and a flexible portion 29. Slidable portion 28 engages the outside diameter of housing 12 and is adapted to slide freely thereon. Accordingly, sleeve 14 is also preferably cylindrically shaped to be compatible with the preferable configuration of the housing. Flexible portion 29, on the other hand, includes a plurality of flexible arms 30 extending toward the distal end of the housing and terminating in inwardly projecting feet 31. There are usually an equivalent number of arms 30 as there are slots 24 in housing 12, with the arms being radially spaced to correspond with the spacing of slots 24 around the periphery of the housing. Accordingly, feet 31 on the flexible arms are adapted to project inwardly through slots 24. In this configuration, feet 31 contact the proximal surface of flange 20 on lancet 18. This engagement occurs more toward the proximal side of slot 24 so that there is room for movement of the feet in a distal direction. At the juncture point between each flexible arm and inwardly projecting foot 31, a tapered surface 32 is preferably formed. This tapered surface is formed so that it slants in an interior direction, and substantially at the same angle as tapered surface 25 in the housing. Therefore, these tapered surfaces 25 and 32, respectively, are adapted to mate with each other.

Instead of being inclined, surface 32 at the end of flexible arm 29 may be rounded. This structure is seen in FIG. 4, wherein rounded surfaces 40 are formed at the distal ends of flexible arms 29a. These rounded edges will reduce the friction between rounded edges 40 and inclined surfaces 25a on housing 12a when sleeve 14a is moved downwardly.

In the manufacture of the retractable lancet assembly of the present invention, housing 12 and sleeve 14 are preferably made of plastic such as polyethylene, whereas coil spring 21 and lancet 18 are preferably made of metal, with the lancet desirably being made out of steel.

Figure 5:
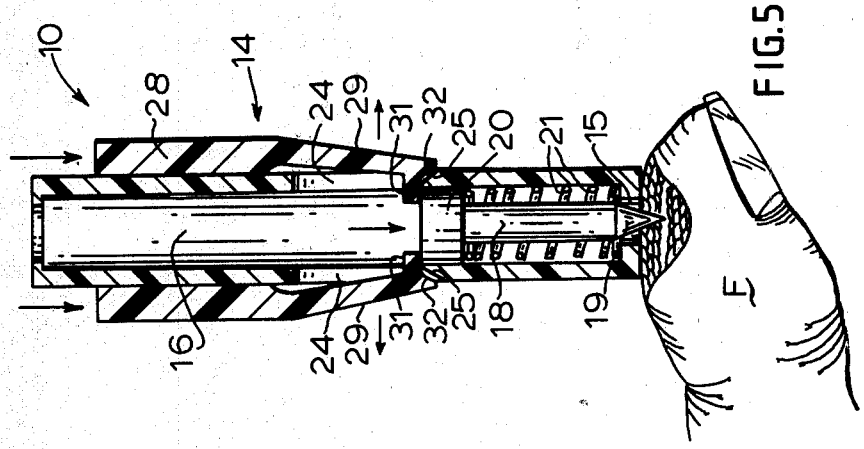
FIG. 5 is a sectional view of the assembly of FIG. 1 illustrating the lancet point penetrating a patient's finger during operation of the assembly.

Turning now to FIG. 5, retractable lancet assembly 10 is illustrated in its operation. A finger F of a patient is positioned under the distal end of the housing so that aperture 15 lies above the finger surface. The operator then grasps slidable portion 28 of sleeve 14 and moves it quickly downwardly (as shown by the arrows) toward the distal end of the housing. This distal movement causes feet 31 to engage flange 20 of the lancet. Therefore, lancet 18 also moves downwardly or distally so that point 19 emerges through aperture 15 and penetrates finger F of the patient. It is noted by referring to FIG. 5 that coil spring 21 is compressed by the distal movement of the flange inside the housing. This illustration also shows the penetration of point 19 into the finger immediately prior to contact between mating inclined surfaces 25 and 32.

Turning now to FIG. 6, the operator of the retractor assembly is still sliding sleeve 14 in a downward or distal direction. In the same continuous motion as that illustrated in FIG. 5, inclined surfaces 32 at the end of flexible arms 29 come in contact with mating inclined surfaces 25 at the distal end of slots 24 in the housing. Continued distal movement causes a shearing action and induces flexible arms 29 to flex outwardly along this shear plane (as illustrated by the outward arrows in FIG. 5). When this happens, all in one rapid movement, feet 31 also move outwardly and become disengaged from the proximal surface of flange 20 of the lacent. With no restraining force on the lancet, coil spring 21, compressed as in FIG. 5, releases its energy thereby rapidly injecting lancet 18 back inside the passageway of the housing. Thus, in one continual downward or distal direction of movement of sleeve 14, lancet 18 is rapidly urged into the finger of the patient and then is rapidly and automatically retracted back inside the housing without a secondardy movement by the operator of this device. Also, after spring 21 releases its energy and becomes non-compressed, its individually coiled rings tend to separate. The resilient nature of arms 29 still maintains an inward bias so that feet 31 project inwardly between the rings of the coil spring. As a result, a jamming effect is produced after use of this lancet assembly so that it cannot be used again to cause contamination.

The axial sliding movement of sleeve 14 over housing 12 is convenient for operation while providing a straightforward assembly for inexpensive manufacture. Furthermore, whereas one continuous movement of the sleeve over the housing causes both outward and inward movement of the lancet, only one spring is required to complete this operation, instead of two springs which some of the prior art devices rely upon. As a result, the present invention provides significant improvements in the procedure of penetrating a patient's skin for small quantities of blood to be collected and analyzed.

What is claimed is:

1. A throw-away automatically retractable spring lancet assembly for piercing human skin which assembly includes means for preventing reuse, characterized by
   (a) a housing having an aperture;
   (b) a plurality of circumferentially spaced elongated openings on said housing;
   (c) a lancet mounted in said housing for reciprocable movement therein;
   (d) a point on said lancet positioned adjacent the interior side of said housing aperture;
   (e) an un-compressed spring in said housing extending between said housing aperture and said lancet;
   (f) a sleeve slidable on said housing;
   (g) a plurality of elongated flexible arms on said sleeve with feet on the arms extending through said plurality of elongated openings and engaging said lancet;
   (h) cooperating means in said openings and on said feet for simultaneously automatically, upon movement of said sleeve over said housing, compressing said spring, moving said lancet point through said housing opening and retracting said lancet point back into said housing; and
   (i) said cooperating means including means for jamming said spring for preventing further movement of said lancet point through said housing opening after the retraction thereof.

2. The assembly of claim 1 wherein said housing is substantially cylindrical.

3. The assembly of claim 1 wherein said spring is a coil spring.

4. The assembly of claim 1 wherein said cooperating means includes mating shear surfaces on said sleeve and said housing to remove said urging force on the lancet after the spring is compressed whereby said spring is allowed to become non-compressed and thereby retract said point back into said housing.

5. The assembly of claim 4 wherein said shear surfaces are mating inclined surfaces on the slidable means and the housing.

6. The assembly of claim 4 wherein the shear surface on said housing is inclind and the shear surface on said slidable means is rounded.

7. The assembly of claim 4, wherein (a) said shear surfaces on said sleeve are at the end of each individual foot on said plurality of flexible arms; and (b) said arms being adapted to flex outwardly after their respective inclined surface engages the cooperating inclined surface on said housing to cause removal of the forward movement against said lancet for retracting said lancet back into said housing.

8. The assembly of claim 1 wherein said feet are adapted to flex inwardly after the lancet is retracted back inside said housing through said elongated openings to cause same to jam the spring thereby preventing re-use of the lancet assembly.

9. The assembly of claim 1, wherein (a) the longitudinal dimension of said plurality of elongated openings and flexible arms automatically determines the depth of penetration of said lancet point through said housing opening.

* * * * *